US00PP09286P

United States Patent [19]

Cole

[11] Patent Number: Plant 9,286

[45] Date of Patent: Sep. 12, 1995

[54] IMPATIENS PLANT NAMED 'RASPBERRY ICE'

[75] Inventor: Douglas S. Cole, Loudon, N.H.

[73] Assignee: D.S. Cole Growers, Inc., Loudon, N.H.

[21] Appl. No.: 262,491

[22] Filed: Jun. 20, 1994

[51] Int. Cl.[6] ..... A01H 5/00

[52] U.S. Cl. ..... Plt./87.6

[58] Field of Search ..... Plt. 87.6

[56] References Cited

U.S. PATENT DOCUMENTS

PP. 8,340 8/1993 Verhoeven ..... Plt./87.6

*Primary Examiner*—James R. Feyrer

*Attorney, Agent, or Firm*—Foley & Lardner

[57] ABSTRACT

A new cultivar of Impatiens plant named Rasberry Ice, characterized by its deep rose flower color, its consistent fully double flowers, and its variegated foliage consisting of a greyed-green main color, and white edges which extend variably from the margin toward the leaf midrib, and an irregular lighter greyed-green color located randomly between the margins and the main tissue, and extending irregularly from the midrib.

1 Drawing Sheet

The present invention comprises a new and distinctive cultivar of Impatiens plant, botanically known as *Impatiens sultanii,* and known by the cultivar named Raspberry Ice. The species name appears to be synonymous with the species designated *Impatiens wallerana,* also referred to in botanical literature.

The new cultivar is a sport or mutation of the cultivar Rosebud ® Rose, and was discovered by the inventor Douglas S. Cole in Jan. 1994 in a greenhouse in Concord, N.H. The mutation was discovered while taking cuttings of the parent cultivar, when one branch of one plant of the parent cultivar displayed variegated foliage, as opposed to the solid green foliage of the parent cultivar. The branch cutting was removed, planted, and grown out, with the variegation and foliage being commonly displayed throughout the plant. Subsequent asexual reproduction by terminal or stem cuttings taken by the inventor in Concord, N.H. has shown that the unique features of this new cultivar are stabilized and are reproduced true to type in successive propagations.

The following characteristics taken in combination distinguish the new cultivar Raspberry Ice from both its parent and the cultivated *Impatiens sultanii* of this type known and used in the floriculture industry:

1. Fully double, consistent blooms.

2. Even growing, well shaped mounded plant habit. Reasonably self-branching if propagated from a vegetative cutting.

3. Rooting time is approximately seven days to initiate roots at 70° F.; salable cuttings are available in 21 days at 70° F.

4. Cuttings are produced from either tips or sections. The highest quality cuttings are produced by removing an approximately 0.5–1.3 cm tip and discarding it. The remaining cutting then branches much better.

5. The main foliage color is greyed-green, surrounded by irregular areas of a lighter greyed-green, and distinct white edges. At times when it is newly potted and growing extremely rapidly the white margin will become thinner and the center of the leaf will have a silver sheen over it.

6. The plant flowers in approximately six weeks from a pinched rooted cutting.

7. When left to reach full bloom, the plant is covered with blossoms which are a deep rose in color.

8. Perhaps the most distinguishing features of Raspberry Ice over other known double Impatiens cultivars are its deep rose double flowers combined with its leaf variegation. The margin variegation is very stable and remains white in color as the plant matures.

The new cultivar is similar in most respects to the parent cultivar Rosebud ® Rose. The primary difference is the leaf variegation of Raspberry Ice. The leaves of the parent cultivar are a solid green. In addition, the new cultivar has a somewhat slower and more dense growth habit. Although leaf variegation also is shown in Peach Ice (U.S. Plant Pat. No. 7,690) and Blackberry Ice (U.S. Plant Pat. No. 8,340), the light variegation color in both of those cultivars is a creamy white, as contrasted to the pure white margins of the new cultivar. In addition, the dark rose flower color of Raspberry Ice is clearly different than the coral and bright red-purple flower color, respectively, the Peach Ice and Blackberry Ice.

The accompanying colored photographs illustrate the overall appearance of the new cultivar, showing the colors as true as it is reasonably possible to obtain in a colored reproduction of this type.

The top photograph is a front view of a fully grown plant of Raspberry Ice.

The bottom photograph is a closeup view showing several flowers and variegated foliage. The illustrated flower color is not precisely shown, and reference is made to the flower color values noted below for the correct color.

The following is a detailed description of my new Impatiens cultivar based on plants produced under commercial practice at Loudon, N.H. Color references are made to The Royal Horticultural Society Colour Chart except where general terms of ordinary dictionary significance are used. The color values were determined during sunny conditions under part natural and part inflorescent light in Washington, D.C.

Parentage: Mutation of *Impatiens sultanii,* c.v. Rosebud ® Rose.

Propagation:

A. *Type cutting.*—Tip or section (section is always near tip).

B. *Time to initiate roots.*—7 days at 21° C. summer, 7 days at 21° C. winter.

C. *Rooting habit.*—Good; roots at nodes or internodes; no hormones needed.

PLANT DESCRIPTION

A. *Form.*—Mounded form, with some spreading and slight hanging when given space.

B. *Habit of growth.*—Slower, denser growth than its green leaved parent.

C. *Foliage.*—Generally speaking, the foliage color is comprised of three colors or shades: green, green with a silver sheen, and a white margin which varies in width, all in varying percentages.

1. *Size (mature leaf).*—Width: 3.0 to 4.0 cm at widest point. Length: Approximately 5.0 to 7.0 cm (excluding petiole).
2. *Shape.*—Ovate, tip acuminate.
3. *Texture.*—Smooth with some wrinkling.
4. *Margin.*—Slightly serrated.
5. *Color.*—Mature foliage, top side green overlaid with shiny greyed-green on surface to provide a grey-green overall effect that is closest to 189A but is not specifically provided for on the R.H.S. Colour Chart; margins of leaves are white 155A and vary in width from the margin; there are random irregular areas of approximately 189B between main leaf tissue and margin, and also extending in certain areas from midrib. The third color (189B) is sufficiently extensive to provide a tricolor effect. On immature foliage, top side is closest to 137A overlaid with 189A to give a more green overall effect than for mature leaves; the marginal variegation is highly variable in width and creamy white 158D in color; these are random and irregular areas of approximately 191B between white variegation and main tissue, and extending to midrib near base. The underside of both mature and immature leaves is closest to 148C, with variegated edges extending throughout but appearing more yellow-white, approximately 158C-D; intermediate color on upper surface is not visible on under surface. The upper surface foliage color of Rosebud® Rose is a solid 137B.
6. *Venation.*—Not distinctive; veins are generally the same color as surrounding tissue, and are alternate.

FLOWERING DESCRIPTION:

A. Flowering habit: Flowers start as a bud the shape of a round ball and the size of a pea, and open similar to a rose in fullness. The flowers open slightly above or even with the foliage, and are carried on stems closest in color to 148B infused with anthocyanin.

B. Flowering season: Year-round in greenhouse environment, best in spring.

C. Flower buds: Basically white with a slight touch of light green 145B-C as bud develops; dark rose color comes out as soon as bud cracks open.

D. Quantity of flowers: Varies as to maturity; good flower producer.

E. Petals: Overall inflorescence has an almost rose or camellia type character due to fully double form.

1. *Shape and size.*—Petals generally round to oval with indentation in tip; mature outer petals approximately 1.5 cm from base to tip and 1.5 to 2.0 cm in width.
2. *Color.*—Upper Surface: Mature, red-purple between 61C and 67C, with slightly darker throat; under surface, light pink at base, with remainder infused with various shades of red-purple.
3. *Number of petals.*—Multiple, twenty-five or even more
4. *Size of flowers.*—3.0 to 4.0 cm in diameter.

F. Spur: Attached to receptacle; approximately 2.0 to 2.5 cm in length, near white at base where attached to receptacle, and light pink approximately 62B-C at tip.

G. Reproductive organs:

1. *Stamens.*—Multiple in number; pollen color yellow.
2. *Pistils.*—Stigma color yellow; styles and ovaries not distinctive.

Disease resistance: Some resistance to Botrytis. Root fungi are seldom a problem.

I claim:

1. A new and distinct cultivar of Impatiens plant named Rasberry Ice, as illustrated and described.

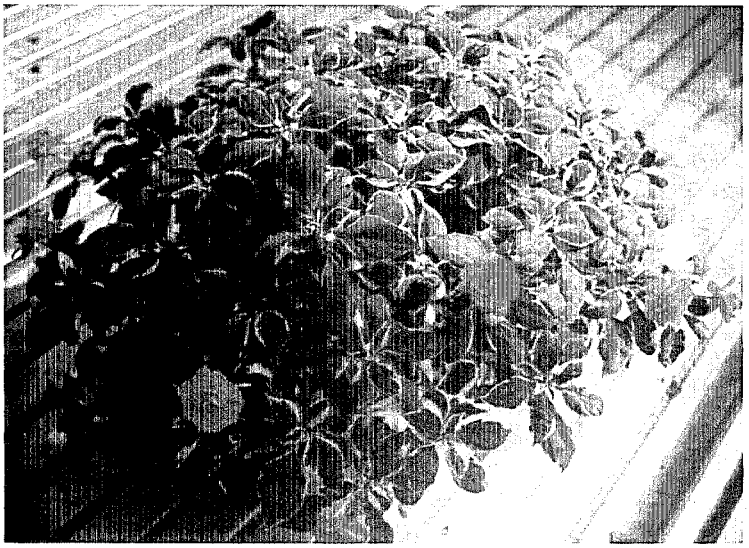
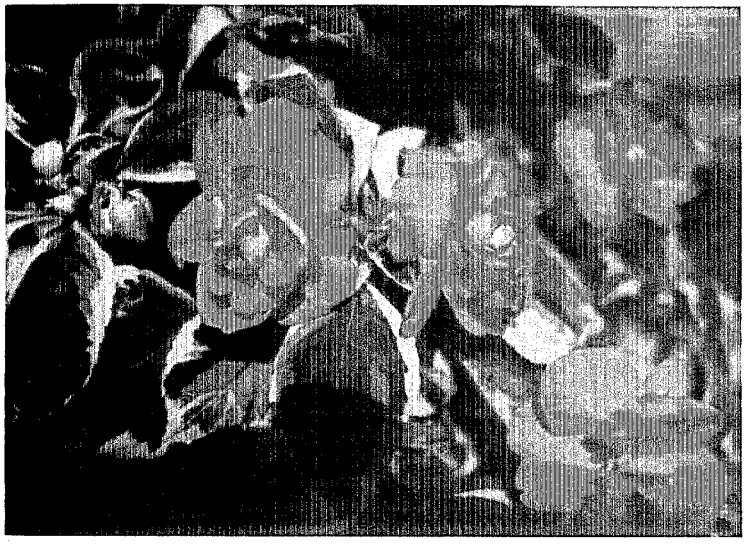

* * * * *